(12) United States Patent  (10) Patent No.: US 7,458,463 B2
Lampropoulos  (45) Date of Patent: Dec. 2, 2008

(54) MEDICAL BIO-WASTE CONTAINER WITH INTEGRATED NEEDLE STOP

(75) Inventor: Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 664 days.

(21) Appl. No.: 10/963,676

(22) Filed: Oct. 13, 2004

(65) Prior Publication Data

US 2006/0079726 A1  Apr. 13, 2006

(51) Int. Cl.
*B65D 83/10* (2006.01)
(52) U.S. Cl. .................................... 206/366
(58) Field of Classification Search ............... 206/366, 206/570, 571, 363, 364, 365, 438, 828; 604/110
See application file for complete search history.

(56) References Cited

U.S. PATENT DOCUMENTS

| 4,936,449 | A | * | 6/1990 | Conard et al. | 206/366 |
| 5,020,665 | A | * | 6/1991 | Bruno | 206/366 |
| 5,024,326 | A | * | 6/1991 | Sandel et al. | 206/366 |
| 5,181,609 | A | * | 1/1993 | Spielmann et al. | 206/370 |
| 5,184,721 | A | * | 2/1993 | Wengyn et al. | 206/366 |
| 5,224,596 | A | * | 7/1993 | Kruger | 206/366 |
| 5,230,426 | A | * | 7/1993 | Keefe et al. | 206/205 |
| 5,311,985 | A | * | 5/1994 | Suida | 206/210 |
| 6,719,017 | B1 | * | 4/2004 | McArthur et al. | 141/86 |
| 7,174,928 | B1 | * | 2/2007 | Lampropoulos | 141/311 A |

* cited by examiner

*Primary Examiner*—Jacob K Ackun, Jr.
(74) *Attorney, Agent, or Firm*—Ryan D. Benson; Stoel Rives, LLP

(57) ABSTRACT

A bio-waste container with integrated needle stop is disclosed. The apparatus includes a catch basin and a waste opening. The catch basin is configured to hold biological and other material, and the waste opening provides an aperture through which such biological and other materials can be deposited in the catch basin during the course of the procedure. The bio-waste container also includes an integrated needle stop apparatus having a cushion layer providing a depository for needles and other sharp tipped objects. The needle stop apparatus further includes a puncture resistant layer which prevents the needles or other sharp tipped objects from penetrating beyond the cushion layer. The needle stop apparatus is secured to the bio-waste container in such a way that it is securely coupled to the bio-waste container during shipping and use, but is selectively removeable from the bio-waste container for separate disposal.

20 Claims, 7 Drawing Sheets

MEDICAL BIO-WASTE CONTAINER WITH INTEGRATED NEEDLE STOP

BACKGROUND OF THE INVENTION

1. The Field of the Invention

Exemplary embodiments of the present invention relate to the field of surgical devices, and, more particularly, to a medical biological waste container with an integrated needle stop component.

2. The Relevant Technology

Millions of surgical procedures are performed in the United States every year. Medical personnel conduct these procedures according to various standards to ensure the health of both the patient and the medical staff. For example, some medical standards are directed to identification and disposal of hazardous waste. Examples of hazardous waste include blood, bodily fluids or the like, and anything contaminated with or containing human blood or other bodily fluids, such as needles, sponges, sheets, etc. Needles and other sharp tipped objects also present a potential hazard in a surgical setting, an emergency room, a patient's room, or in other medical settings.

Specialized procedures are utilized to ensure the safety of the individual, other patients and the rest of the staff. Currently, medical personnel dispose of the needles and other sharp tipped objects separately from other waste materials, such as sponges, etc. A needle stop device is often used to temporarily store and later to dispose of these needles and other sharp tipped objects. In a surgical setting, the needle stop device may be located on the operating table, or on another table or surface adjacent the operating table. In an emergency room, the needle stop device may be located on a cart or other accessory positioned near the patient.

One example of a typical needle stop device is a container, surface or layer having some material into which a needle can be inserted. This material helps secure the needle while the medical professional removes the syringe. Rigid, compressible or resilient foam can be used for this purpose, although other materials are also suitable. During set up for a medical procedure, and during the procedure, it is common for medical personnel to place needles, syringes and other sharps in a needle stop device so that they are easily accessible during the procedure. Then, when the surgery or emergency procedure is completed, the needle stop device containing all of the needles used in the procedure is disposed of as a unit, so that no further handling of the needle or exposure of the needle tip is needed. This helps alleviate the possibility of medical personnel accidentally puncturing, contaminating, or otherwise exposing themselves to the used needle.

In addition to the needle stop device currently employed, a hazardous or biological waste container is also located somewhere near the patient in the operating room. This container is used to dispose of contaminated materials such as sponges, dressings, etc. that are contaminated with a patients bodily fluids or that are otherwise used during the procedure. Medical personnel can then dispose of this container as a unit at the end of the surgery to minimize the amount of human contact with the waste.

One problem with this system is that operating room and emergency room personnel must constantly watch for the different containers/devices to ensure that appropriate waste is disposed of in appropriate containers. With so many instruments and other medical accoutrements associated with surgical or emergency procedures occupying a limited amount of space, there is great potential for the hazardous waste disposal containers to be misplaced, covered, or accidentally knocked on the floor. This can require time consuming and inconvenient disposal and replacement of the containers during the procedure. Such additional time can be important during time sensitive procedures both from a safety and cost standpoint.

BRIEF SUMMARY OF THE INVENTION

Exemplary embodiments of the present invention are directed to a bio-waste container having an integrated needle stop device. This provides one easy, convenient package that provides medical personnel with a single place to dispose of all medical waste, regardless of type. When the medical procedure is concluded, medical personnel can dispose of the needle stop device separately from the other bio-waste, by simply optionally separating the needle stop device from the bio-waste container.

One exemplary embodiment of a bio-waste container according to the present invention includes a catch basin and a waste opening. The catch basin is configured to hold biological and other material, while the waste opening provides an aperture through which such biological and other materials can be deposited in the catch basin during the course of the procedure. The bio-waste container further comprises a needle stop apparatus providing a depository for needles and other sharp tipped objects. The needle stop apparatus comprises a cushion layer into which needles and other sharp tipped objects can be inserted. The cushion layer secures the needles and other sharp tipped objects during the procedure. The needle stop apparatus also includes a puncture resistant layer which prevents the needles or other sharp tipped objects from penetrating beyond the cushion layer. The puncture resistant layer prevents any needles or other sharps stored in the needle stop component from penetrating into the bio-waste container and thereby safeguards such needles and other sharps from possible contamination by any bio-waste materials that may be located in the interior of the bio-waste container. Finally, a securement apparatus engages an external surface of the needle stop apparatus such that the needle stop apparatus remains fixed relative to the catch basin during the course of the procedure, while allowing the user to selectively detach at least a portion of the needle stop apparatus from the bio-waste container and discard the needle stop apparatus separately from the catch basin.

In one exemplary embodiment, the cushion layer is made from a compressible, rigid or resilient foam. In another embodiment, the securement apparatus is a piece of plastic that surrounds the foam and that holds the needle stop apparatus securely against the catch basin. Alternately, the securement apparatus can be an adhesive that holds the cushion layer securely against the catch basin until the procedure is ended. In still other embodiments, a hook and loop type device (such as Velcro®) or a clip can be used to hold the needle stop apparatus securely against the catch basin. A tab can be attached to the cushion layer or to the securement apparatus to facilitate the removal of the needle stop apparatus from the catch basin. This allows the needles to be disposed of separately from other biological waste while minimizing the handling of the used needles.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE EXEMPLARY EMBODIMENTS

Exemplary embodiments of the present invention provide a medical bio-waste container with an integrated needle stop component. One exemplary embodiment of a bio-waste container according to the present invention includes a catch basin and a waste opening. The catch basin is configured to hold biological and other material, while the waste opening provides an aperture through which such biological and other materials can be deposited in the catch basin during the course of the procedure. The bio-waste container further comprises a needle stop component providing a depository for needles and other sharp tipped objects. The needle stop apparatus comprises a cushion layer into which needles and other sharp tipped objects can be inserted. The cushion layer secures the needles and other sharp tipped objects during the procedure. The needle stop apparatus also includes a puncture resistant layer which prevents the needles or other sharp tipped objects from penetrating beyond the cushion layer. The puncture resistant layer prevents any needles or other sharps stored in the needle stop component from penetrating into the bio-waste container and thereby safeguards such needles and other sharps from possible contamination by any bio-waste materials that may be located in the interior of the bio-waste container. Finally, a securement apparatus engages an external surface of the needle stop apparatus such that the needle stop apparatus remains fixed relative to the catch basin during the course of the procedure, while allowing the user to selectively detach at least a portion of the needle stop from the bio-waste container and discard the needle stop apparatus separately from the catch basin.

For the illustrated embodiments shown below, the terms hazardous waste, bio-waste, and biological waste are used synonymously to include any type of medical waste or waste product that requires special handling, i.e. that requires incineration, or disposal by some other means known to those of skill in the art.

Figure 1:
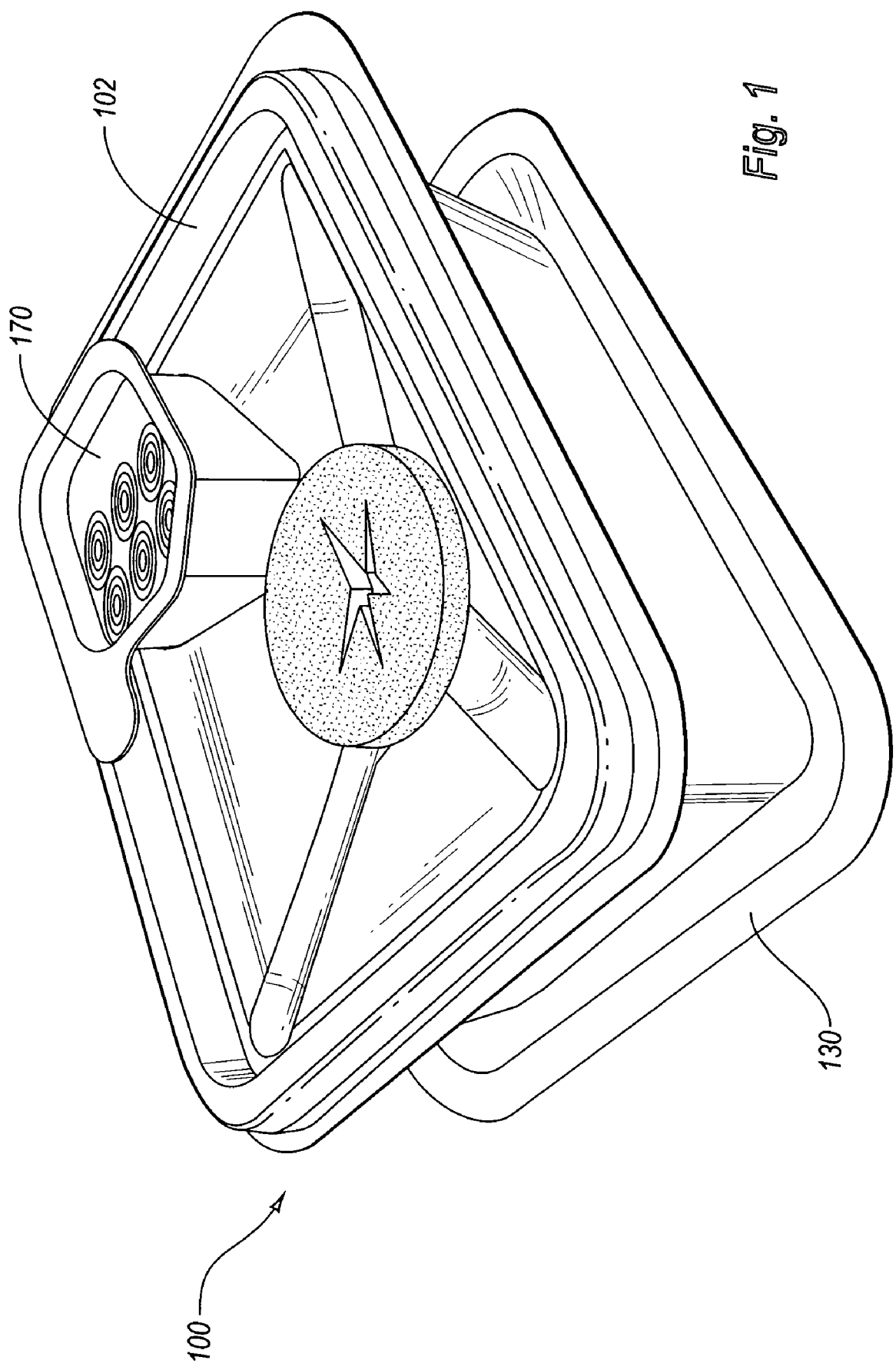
FIG. 1 illustrates a perspective view of one exemplary embodiment of a bio-waste container with an integrated needle stop device according to the present invention.
Figure 2:
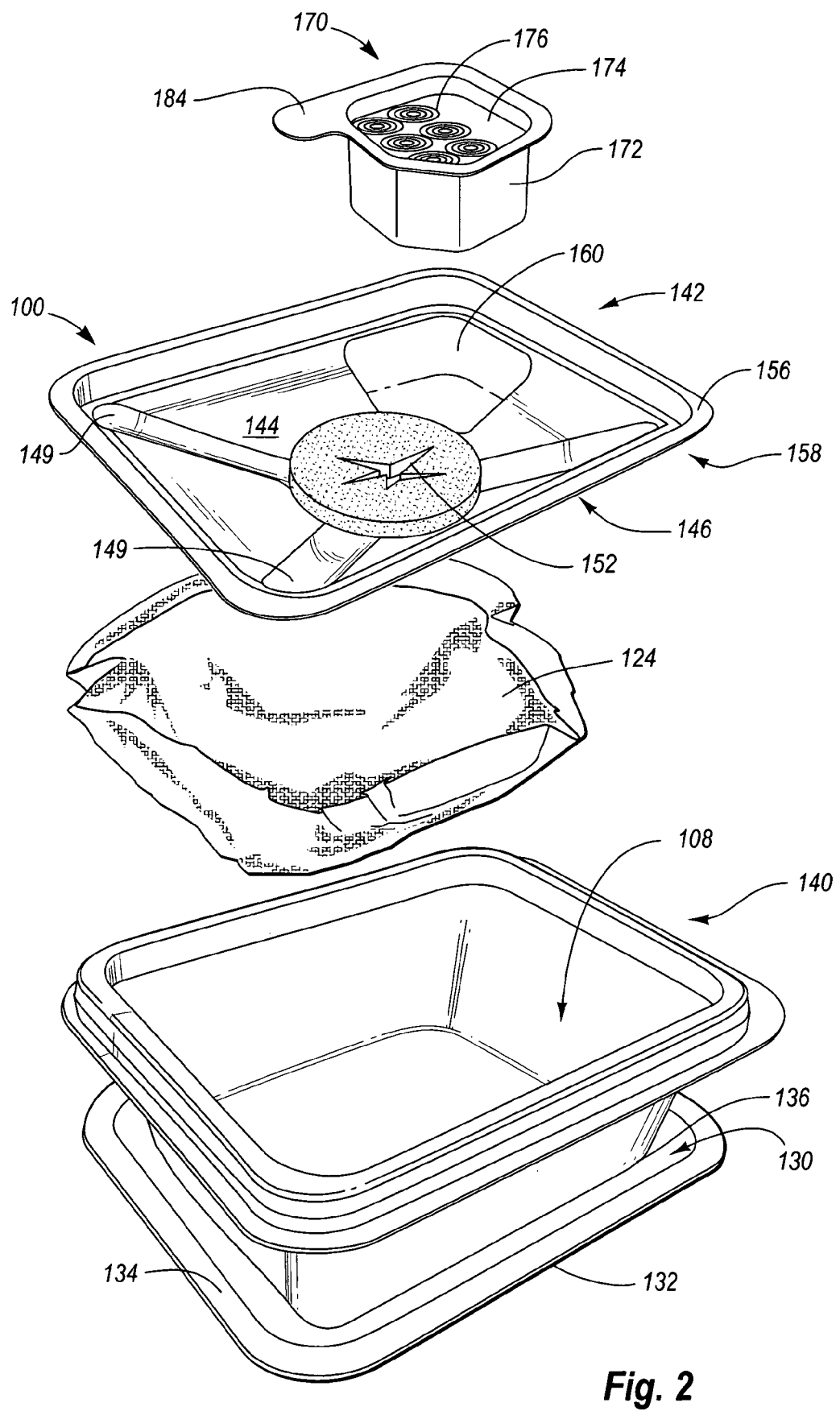
FIG. 2 illustrates an exploded perspective view of the components of the bio-waste container of FIG. 1.
Figure 3:
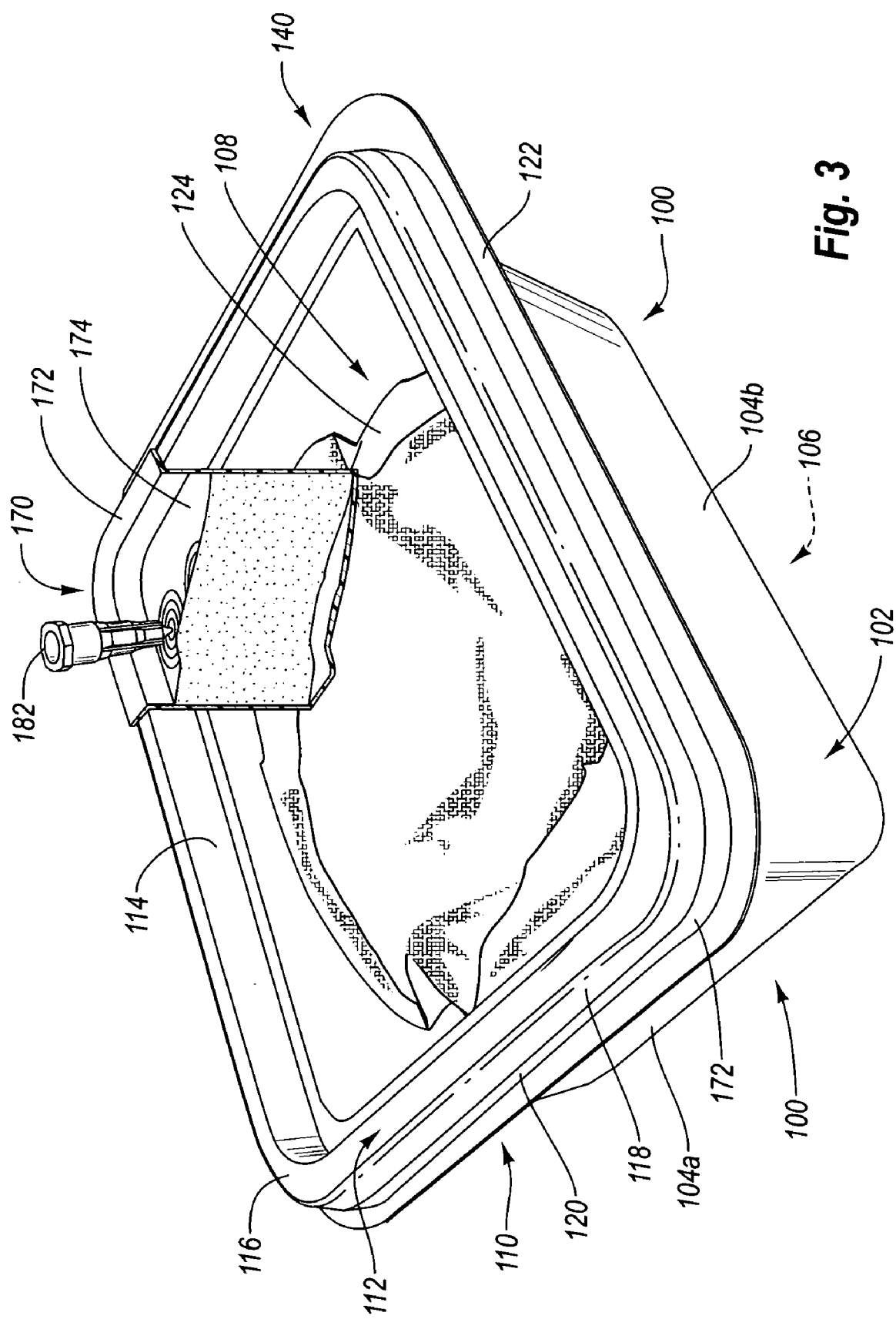
FIG. 3 illustrates the positioning of the needle stop device relative to the cover assembly used in the bio-waste container of FIG. 1.

FIGS. 1-3 illustrate one exemplary embodiment of a bio-waste disposal container with an integrated needle stop component, designated generally as reference numeral 100. As illustrated in FIG. 1, apparatus 100 preferably has three main components, namely, a container portion 102, a lid 130 and a needle stop component 170. Container portion 102 provides an enclosed container for disposal of bio-waste materials, such as used surgical pads, sponges, etc. The integrated needle stop component 170, which in this embodiment nests in a recess formed in one corner of container portion 102, provides a convenient location for storage of needles, syringes and other sharps during set up and performance of a medical procedure.

Following completion of a medical procedure, needle stop component 170 may optionally be separated from container portion 102 and disposed of separately if the applicable disposal protocol so dictates. Alternatively, the entire apparatus 100, including needle stop component 170, can be disposed of as a single unit if the applicable disposal protocol permits.

As discussed in more detail below, lid 130 is formed with a recess that is configured to accept a bottom portion of container portion 102 in a press-fit, nesting relationship during use of apparatus 100, as depicted in FIGS. 1 and 3. Lid 130 is also configured to fit over and engage the top portion of container portion 102. When it is time to dispose of apparatus 100, lid 130 is separated from the bottom of container portion 102 and is pressed into place over the top of container portion 102, with or without needle stop component 170 in place in container portion 102.

In this manner, apparatus 100 provides a single location for both bio-waste and sharp tipped objects. Apparatus 100 allows operating room personnel to control both needles and other bio-waste in a single container. The device can be centrally located to provide access to all medical personnel and is thus conveniently available within the operating room. Using apparatus 100, medical personnel need no longer look to multiple locations to dispose of bio-waste and sharp tipped objects, thus saving time and eliminating confusion in an otherwise hectic setting.

Referring now to FIGS. 2 and 3, container portion 102 comprises four side walls 104a-d and a bottom 106 that define a catch basin 108. Container portion 102 further includes a top section 110 that extends around the perimeter of container portion 102. Container portion 102 and top section 110 define in interior space into which bio-waste and other materials can be deposited. In this exemplary embodiment, the top section 110 is integrally formed as part of container portion 102. However, the top section 110 could also be a separate piece attached by various means to the container portion 102. The top section 110 includes a ridge 112 that projects upwardly, and a lip 122 that extends generally horizontally out from ridge 112. In one embodiment, the lip 122 provides a support base for the cover assembly 140. Additionally, the lip 122 can provide a support base for a lid 130 that is used to seal container portion 102 after the completion of a medical procedure. In some embodiments, additional absorbent material 124 can be located within catch basin 108 of container portion 102 to absorb liquid or semi-liquid materials.

The ridge 112 includes an inside surface 114 and a top surface 116. The top surface 116 provides further support for cover assembly 140. The ridge 112 also includes an upper outside portion 118 and a lower outside portion 120. In the embodiment shown, upper outside portion 118 extends slightly outwardly from the vertical, while lower outside portion 120 extends slightly inwardly from the vertical. This design optionally allows cover assembly 140 and lid 130 to be snap fit over ridge 112, thus providing a secure attachment without the need for mechanical or other fasteners. In alternate embodiments, cover assembly 140 rests directly on top surface 116 (see, e.g., FIG. 4).

As best shown in FIG. 2, container cover 142 of cover assembly 140 includes an upper surface 144 and a lower surface 146. The container cover also includes an opening 148 that provides for access to catch basin 108. In one exemplary embodiment, opening 148 is located approximately in the center of container cover 142. Additionally, the upper and lower surfaces 144, 146 may slope towards the middle of container portion 102 to facilitate the flow of liquids into catch basin 108 of container portion 102. One or more channels 149 can be integrated into container cover 142 to facilitate this flow.

The catch basin 108 stores the bio-waste material during the surgical procedure, and segregates this material from the rest of the room and from needle stop device 170, thus limiting contamination of operating or emergency room surfaces and/or personnel. The opening 148 can include a flexible porous material 150 having slits 152 that allow waste material to be inserted into, and that hold such material within, catch basin 108. The flexible porous material 150 also facilitates the absorption of excess fluids that could contaminate the operating area.

Referring to FIGS. 2 and 3, container cover 142 can include a top surface 156 and a lower outside surface 158. When the cover assembly 140 is secured over container portion 102, top surface 156 contacts top surface 116 and lower outside surface 158 contacts inside surface 114 of container portion 102. This enables cover assembly 140 to nest within container portion 102 without the need for fasteners of any sort.

With further reference to FIG. 2, cover assembly 140 also includes in one corner a recess 160 configured to receive needle stop component 170 in a press-fit, nesting relationship. The shape and dimensions of recess 160 are chosen to be complementary of the overall shape and size of needle stop component 170 so that needle stop component 170 fits securely within recess 160.

As discussed previously, apparatus 100 also includes an integrated needle stop component 170. As illustrated in FIGS. 1-3, needle stop device 170 is removably integrated into cover assembly 140. During set up for a medical procedure, needles, syringes and other sharps can be placed in needle stop component 170 for storage and to provide ready access to such items during the procedure. As needles are used during the surgical procedure, they may also be returned to needle stop device 170 for further storage and/or ultimately for disposal. When the procedure is completed, the entire needle stop device 170, or a portion of needle stop device 170 containing the used needles, can be removed from cover assembly 140 and disposed of separately from the material contained within container portion 102.

Needle stop device 170 comprises a generally cup-shaped hard plastic shell 172 and a cushion layer 174 positioned within shell 172. The material forming shell 172 is preferably selected to provide a puncture resistant layer that prevents a needle assembly 182 or other sharp tipped objects from penetrating beyond cushion layer 174. This puncture resistant layer prevents needles and other sharps inserted into needle stop component 170 from inadvertently penetrating into the interior of waste container portion 102 and thereby preventing contamination of such needles and other sharps by any waste material contained therein. In this exemplary embodiment, needle stop component 170 is configured to fit in one corner of container portion 102 and to nest within recess 160 as illustrated. Other shapes for needle stop component 170 can also be used depending on the shape of container portion 102.

In exemplary embodiments, cushion layer 174 can be a rigid, compressible or resilient foam, such as, but not limited to, styrofoam, that is dense enough to hold needle assembly 182 while a syringe (not shown) or other structure is removed from needle assembly 182. This leaves the needle assembly 182 securely retained within cushion layer 174. In addition, the material forming cushion layer 174 is preferably selected so that it has sufficient structural integrity that it is "non-coring." More specifically, when medical needles are inserted into and removed from needle stop component 170, cushion layer 174 preferably has sufficient structural integrity that a core of material will not be torn away from cushion layer 174 and remain within the lumen of the needle as the needle is withdrawn.

As best illustrated in FIGS. 1 and 2, cushion layer 174 preferably includes one or more target symbols 176 printed on the its upper surface. Target symbols 176 not only provide a visible cue or indicator to operating personnel that needle stop 170 is intended to store needles and other sharps, but it also assists medical personnel in spacing multiple needles and other sharps apart from one another to further enhance accessibility of such needles and other sharps during the conduct of a medical procedure.

The needle stop device 170 also includes a tab 184 that a user can grip to remove needle stop device 170 from cover assembly 140. In the embodiment illustrated in FIGS. 1-3, tab 184 is integrally formed as part of shell 172. Additionally, a user can selectively detach all or a portion of needle stop device 170 when the procedure is completed.

Needle stop component 170 can be removeably secured to container portion 102 by various means. In the embodiment illustrated in FIGS. 1-3, needle stop component 170 engages recess 160 formed in one corner of cover assembly 140 and is removably secured to container portion 102 using a close tolerance, snap-fit arrangement. This close tolerance, snap-fit arrangement constitutes one means for selectively securing needle stop component 170 to container portion 102. Other means for selectively securing needle stop component 170 to container portion 102 are disclosed in connection with the embodiments illustrated in FIGS. 4-7 and described below. However, the illustrated means for selectively securing needle stop component 170 to container portion 102 are not intended to be exhaustive, and other suitable securement means, devices, methods and/or mechanisms known to those skilled in the art may be substituted without departing from the scope and intent of the present invention.

Container cover 142 and needle stop device 170 can form separate and independent parts of cover assembly 140. This lets a user pull tab 184 and easily disengage needle stop device 170 from cover assembly 140. This disengagement allows the used needle assemblies 182 to be discarded separately from the rest of the medical waste contained within catch basin 108.

Regardless of how container cover 142 and needle stop device 170 are integrated, the puncture resistant layer can be removed either separately or along with cushion layer 174. In either case, when the needle stop device containing the used needles is removed, lid 130 can be secured over, for example, ridge 112 of container portion 102 to hold the contents of catch basin 108 securely within container portion 102. This prevents unwanted spillage and provides a simple, effective way for medical personnel to dispose of the medical waste without further human contact.

The lid 130 is designed to fit tightly over container portion 102 when needle stop device 170 is removed. The lid 130 includes a first recess 132 that is sized to securely fit over ridge 112. A lip 134 is disposed about a periphery of the lid 130. The lip 134 contacts lip 122 of container portion 102. The lid can optionally include a second recess 136 that is sized to mate with bottom 106 of container portion 102, thus preventing the lid from becoming lost when device 100 is in use in the operating room.

In exemplary embodiments of the present invention, the container portion 102, cover assembly 140, and lid 130 are all made from some type of plastic. Such plastics may include, by way of example and not limitation, polyvinyl chloride (PVC), or other suitable materials that are well known to those skilled in the art.

A variety of types and configurations of apparatus 100 can be utilized without departing from the scope and spirit of the present invention. For example, while container portion 102 is shown in the exemplary embodiment as having a generally square rectangular-section with rounded corners, this need not be the case. Any cross section that defines a main compartment of suitable size to hold a desired amount of biowaste is contemplated to fall within the scope of the exemplary embodiments of the present invention. Examples of such cross sections can include, but are not limited to, rectangular, circular, oval, triangular, and/or tetrahedonal. Likewise, while the device illustrated in FIGS. 1-3 has dimensions of approximately 4 inches by 5 inches, many other dimensions are also possible, depending on the desired shape and amount of bio-waste anticipated for the specific procedure being conducted.

In other alternate embodiments, cover assembly 140 could have a downward facing projection (not shown) that contacts inside surface 114 of ridge 112 along at least a portion of the perimeter, thus securing cover assembly 140 in place. In still other alternate embodiments, a projection (not shown) on cover assembly 140 could be bent around lip 122 to secure cover assembly 140 in place. In yet another alternate embodiment, adhesives could be used in addition to or instead of the various methods discussed above. Those skilled in the art will realize that there are many structures and methods that could be employed to secure cover assembly 140 to container portion 102. Any structure or method that secures the two pieces together, or that maintains physical contact between the two pieces, including the force of gravity, is contemplated to fall within the scope of the exemplary embodiments of the present invention.

In one embodiment, other materials besides the foam described above can be used for cushion layer 174. Examples of these other materials can include, but are not limited to, rubber, plastics, or other types of foam. As long as the material grips needle assembly 182 with sufficient force to allow the syringe or other structure to be disengaged from the needle assembly, is it contemplated to fall within the scope of the exemplary embodiments of the present invention.

In one exemplary embodiment, cover assembly 140 "snap fits" over top section 110 of container portion 102. The cover assembly 140 is thus secured to container portion 102, requiring some amount of force to overcome the resistance provided by the interlocking ridges 112, 154. Alternately, cover assembly 140 nests within container portion 102 without being mounted to container portion 102. In either case, lid 130 can be used to secure the container once needle stop apparatus 170 has been removed.

Figure 4:
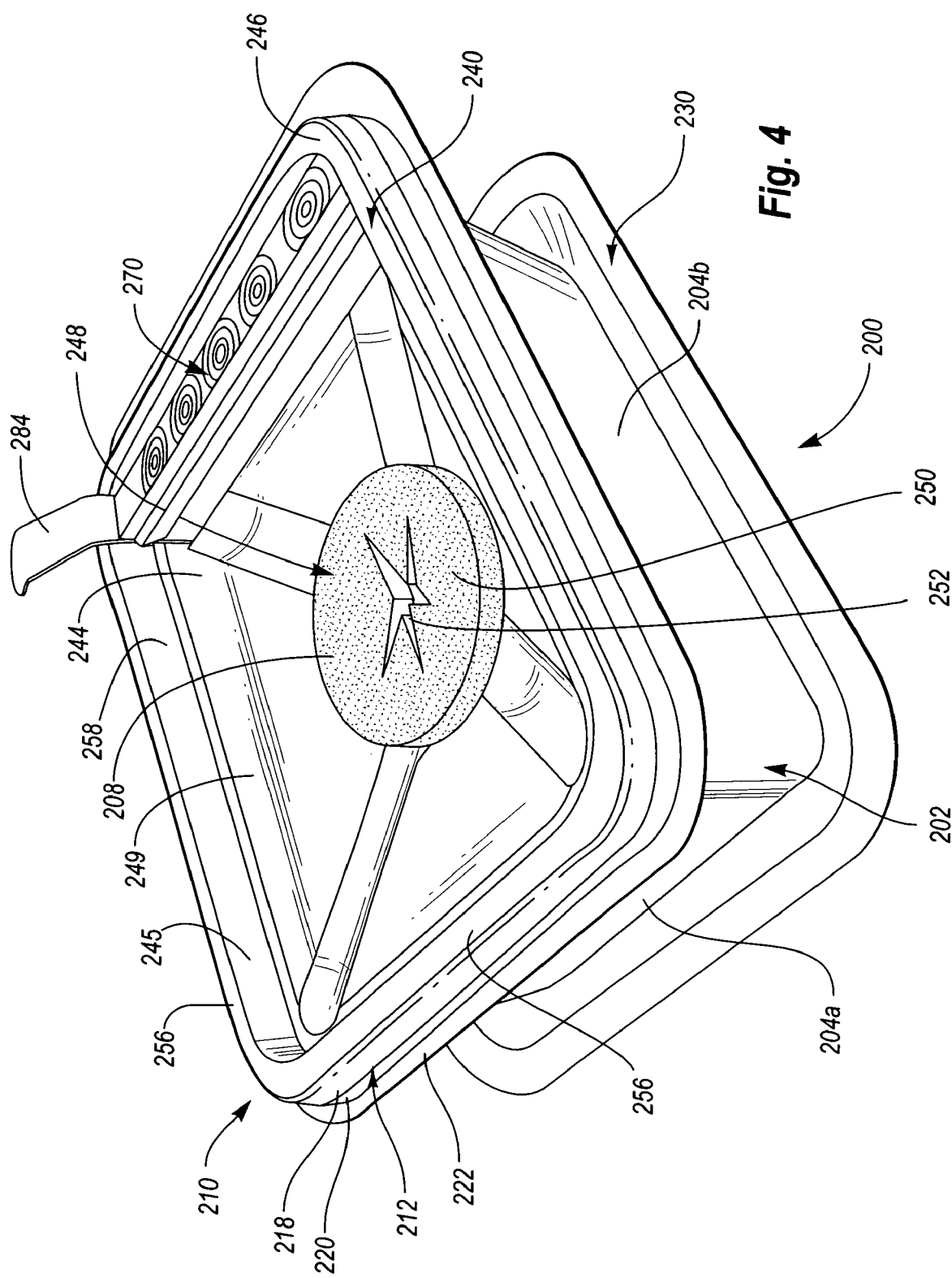
FIG. 4 illustrates a perspective view of an alternate exemplary embodiment of a bio-waste container with an integrated needle stop device according to the present invention.
Figure 5:
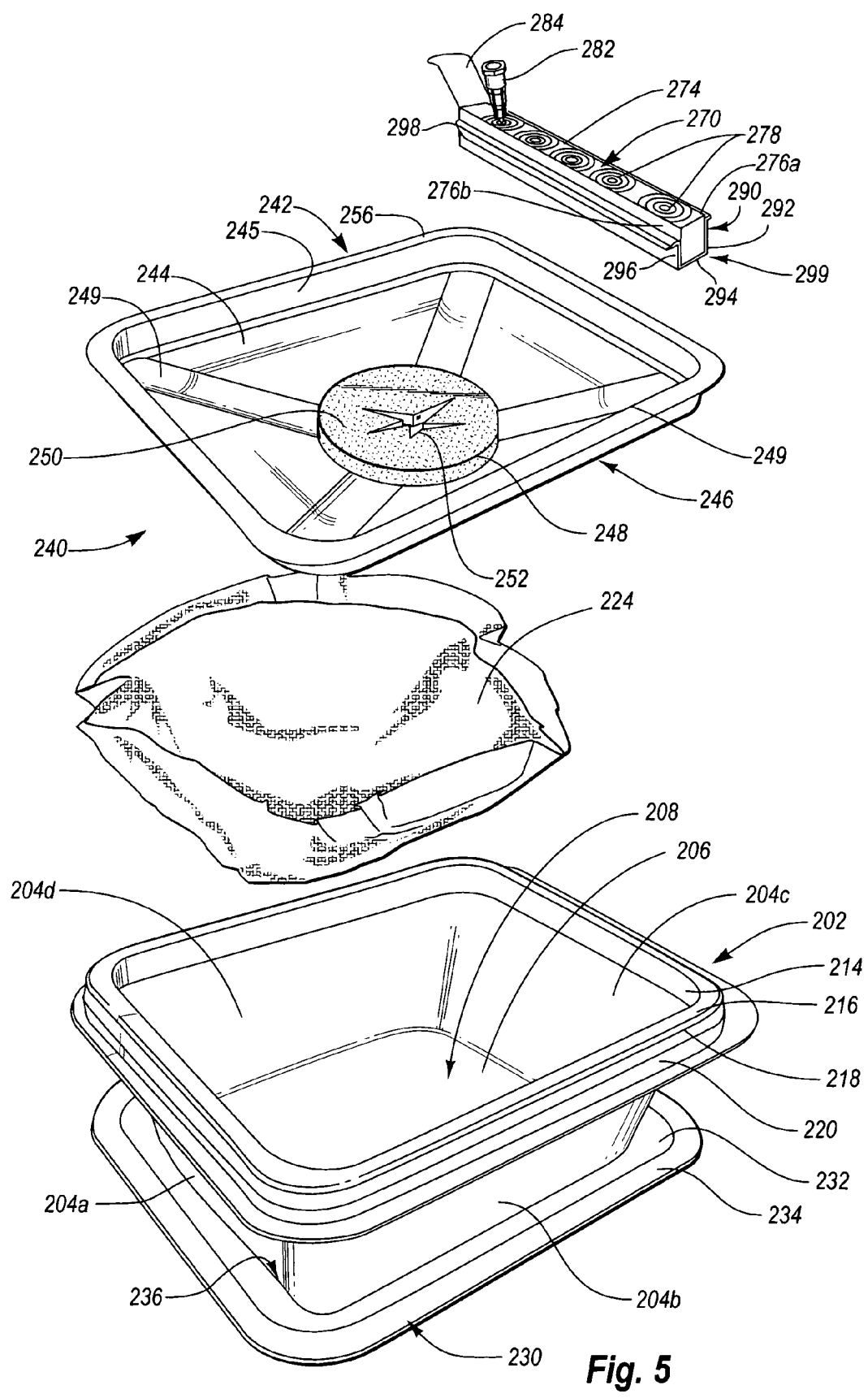
FIG. 5 illustrates an exploded perspective view of the components of the bio-waste container of FIG. 4.

FIGS. 4 and 5 illustrate an alternate exemplary embodiment of a bio-waste disposal apparatus with an integrated needle stop device, designated generally as reference numeral 200. Apparatus 200 includes a container portion 202, and a cover assembly 240. Cover assembly 240 includes a container cover 242 having a needle stop device 270 secured therein. Needle stop device 270 is secured to other components of apparatus 200 to maintain needle stop device 270 adjacent the aperture of the bio-waste container. This provides a single location for both bio-waste and sharp tipped objects. Apparatus 200 allows operating room and other personnel to control both contaminated needles and other bio-waste within a single container while a procedure is ongoing. The apparatus can be centrally located to provide access to all medical personnel and is thus conveniently available within the operating or treatment room. Using apparatus 200, medical personnel need no longer look to multiple locations to dispose of bio-waste and sharp tipped objects, thus saving time and eliminating confusion in an otherwise hectic setting.

The container portion 202 comprises four sides 204a-d and a bottom 206 that define a catch basin 208. The container portion 202 further includes a top section 210 that extends around the perimeter of container portion 202. However, top section 210 could also be a separate piece attached by various means to container portion 202. The top section 210 includes a ridge 212 that projects upwardly, and a lip 222 that extends generally horizontally out from container portion 202. In this exemplary embodiment, lip 222 provides a support base for a lid 230 that is used to seal container portion 202 after the completion of a surgical procedure. In some embodiments, additional absorbent material 224 can be located within catch basin 208 of container portion 202 to absorb liquid or semi-liquid materials.

The ridge 212 includes an inside surface 214 and a top surface 216. The top surface 216 provides support for cover assembly 240. The ridge 212 also includes an upper outside portion 218 and a lower outside portion 220. In the embodiment shown, upper outside portion 218 extends slightly outwardly from the vertical, while lower outside portion 220 extends slightly inwardly from the vertical. This design allows lid 230 to be snap fit over ridge 212, thus providing a secure attachment without the need for mechanical or other fasteners.

As best shown in FIG. 5, the container cover 242 of cover assembly 240 includes an upper surface 244, a lower surface 246, and an inside vertical surface 245. The inside vertical surface 245 contacts inside surface 214 of container portion 202 when cover assembly 240 is installed. The container cover also includes an opening 248 that provides for access to catch basin 208. In one exemplary embodiment, opening 248 is located approximately in the center of container cover 242. Additionally, the upper and lower surfaces 244, 246 may slope towards the middle of container portion 202 to facilitate the flow of liquids into catch basin 208 of container portion 202. The catch basin 208 stores the bio-waste material during the surgical procedure, and segregates this material from the rest of the room and from needle stop device 270, thus limiting contamination of operating or emergency room surfaces and/or personnel. The opening 248 can include a flexible porous material 250 having slots 252 that allow waste material to be inserted into, and that hold such material within, catch basin 208. The flexible porous material 250 also facilitates the absorption of excess fluids that could contaminate the treatment area.

Container cover 242 has a flared portion 256 around its circumference. The flared portion 256 is configured to contact top surface 216 of ridge 212, while inside vertical surface 245 contacts inside surface 214 of container portion 202. The container cover 242 is thus secured within, and rests on top of, container portion 202. In alternate embodiments, container cover 242 can have a mating ridge (not shown) that is configured to fit over ridge 212 of container portion 202, similar to the design described with reference to FIGS. 1-3.

In the exemplary embodiment illustrated in FIGS. 4 and 5, needle stop device 270 is removably integrated into cover assembly 240 using a securement apparatus 290. With specific reference to FIG. 5, securement apparatus 290 is a shell that includes a first side 292, a bottom 294, a second side 296 and a curved portion 298 extending from second side 296. The curved portion 298, second side 296, and first side 292 define a channel 299 that holds needle stop device 270. In this exemplary embodiment, securement apparatus 290 can be attached to container cover 242 using, for example, an adhesive. As needles or other sharp objects are used during a procedure, they are disposed of in needle stop device 270. When the procedure is completed, the entire needle stop device 270, or a portion of needle stop device 270 containing the used needles, can be removed from cover assembly 240 and disposed of separately from the material contained within container portion 202.

The needle stop device 270 comprises a cushion layer 272. The cushion layer 272 includes a top surface 274, and left and right side surfaces 276a and 276b. In this exemplary embodiment, one or more targets 278 are provided on top surface 274 to assist a user with placing a needle assembly 282 into cushion layer 272. A lower surface (not shown) of cushion layer 272 can sit on top of bottom 294 of securement apparatus 290. The bottom 294 then provides a puncture resistant layer which prevents a needle assembly 282 or other sharp tipped objects from penetrating beyond cushion layer 272.

The needle stop device 270 also includes a tab 284 that a user can grip to remove needle stop device 270 from securement apparatus 290. This tab 284 can engage, for example, left or right side surfaces 276a, 276b of cushion layer 272 such that needle stop device 270 remains fixed to securement apparatus 290, which is fixed to container portion 202, during the course of a medical procedure. Additionally, a user can selectively detach all or a portion of needle stop device 270 when the procedure is completed. Alternately, the tab 284 can be connected to securement apparatus 290, so that both securement apparatus 290 and needle stop device 270 can be removed and disposed of as a unit. In either case, this lets a user pull tab 284 and easily disengage all or a portion of needle stop device 270 from cover assembly 240. This disengagement allows the used needle assemblies 282 to be discarded separately from the rest of the medical waste contained within catch basin 208. This is necessary because the needles are disposed of in medical waste that may be taken, for example, to a secure landfill, while the other medical waste can be incinerated at a medical waste destruction facility.

In exemplary embodiments, cushion layer 272 can be a rigid, compressible or resilient foam, such as, but not limited to, Styrofoam, that is dense enough to hold needle assembly 282 while a syringe (not shown) or other structure is removed from needle assembly 282. This leaves needle assembly 282 securely retained within cushion layer 272.

FIG. 5 illustrates one exemplary embodiment of lid 230 in a useful storage position under catch basin 208. The lid 230 is designed to fit over ridge 212 to secure the contents stored in catch basin 208 when needle stop device 270 is removed. The lid 230 includes a first recess 232 that is sized to securely fit over ridge 212. A lip 234 is disposed about a periphery of lid 230. The lip 234 contacts lip 222 of container portion 202. The lid can optionally include a second recess 236 that is sized to mate with bottom 206 of container portion 202, thus preventing the lid from becoming lost when device 200 is in use in the operating room.

While container portion 202 is shown in the exemplary embodiment as having a generally rectangular cross-section, this need not be the case. Any cross section that defines a catch basin 208 of suitable size to hold a desired amount of bio-waste is contemplated to fall within the scope of the exemplary embodiments of the present invention. Examples of such cross sections can include, but are not limited to, square, circular, oval, triangular, and/or tetrahedonal. Likewise, while the illustrated device has dimensions of approximately 5 inches by 7 inches, many other dimensions are also possible. Dimensions of 15 inches by 21 inches or larger can be used, depending on the amount of bio-waste anticipated for the specific surgical or emergency procedure being conducted.

In alternate embodiments, needle stop device 270 need not include a puncture resistant layer, such as bottom 294 of securement apparatus 290. In this case, cushion layer 272 can be directly attached to top surface 244 of container cover 242. The top surface 244 then acts as a puncture resistant layer (See, e.g. FIGS. 6 and 7). In other alternate embodiments, securement apparatus 290 can include perforations in cover assembly 240 that allow needle stop device 270 and securement apparatus 290 to be removed as a unit. Alternately, the securement apparatus can be an adhesive that holds needle stop device 270 in contact with container cover 242. In this alternate embodiment, securement apparatus 290 shown in FIG. 5 would not be used.

In any case, when needle stop device 270 containing the used needle assemblies 282 is removed, lid 230 can be secured over, for example, ridge 212 of container portion 202 to hold the contents of catch basin 208 securely within container portion 202. This prevents unwanted spillage and provides a simple, effective way for medical personnel to dispose of the medical waste without further human contact.

In still other alternate embodiments, cushion layer 272 can be made from other materials, such as, but not limited to, rubber, plastics, or other types of foam. As long as the material grips needle assembly 282 with sufficient force to allow the syringe or other structure to be disengaged from the needle assembly, is it contemplated to fall within the scope of the exemplary embodiments of the present invention.

Figure 6:
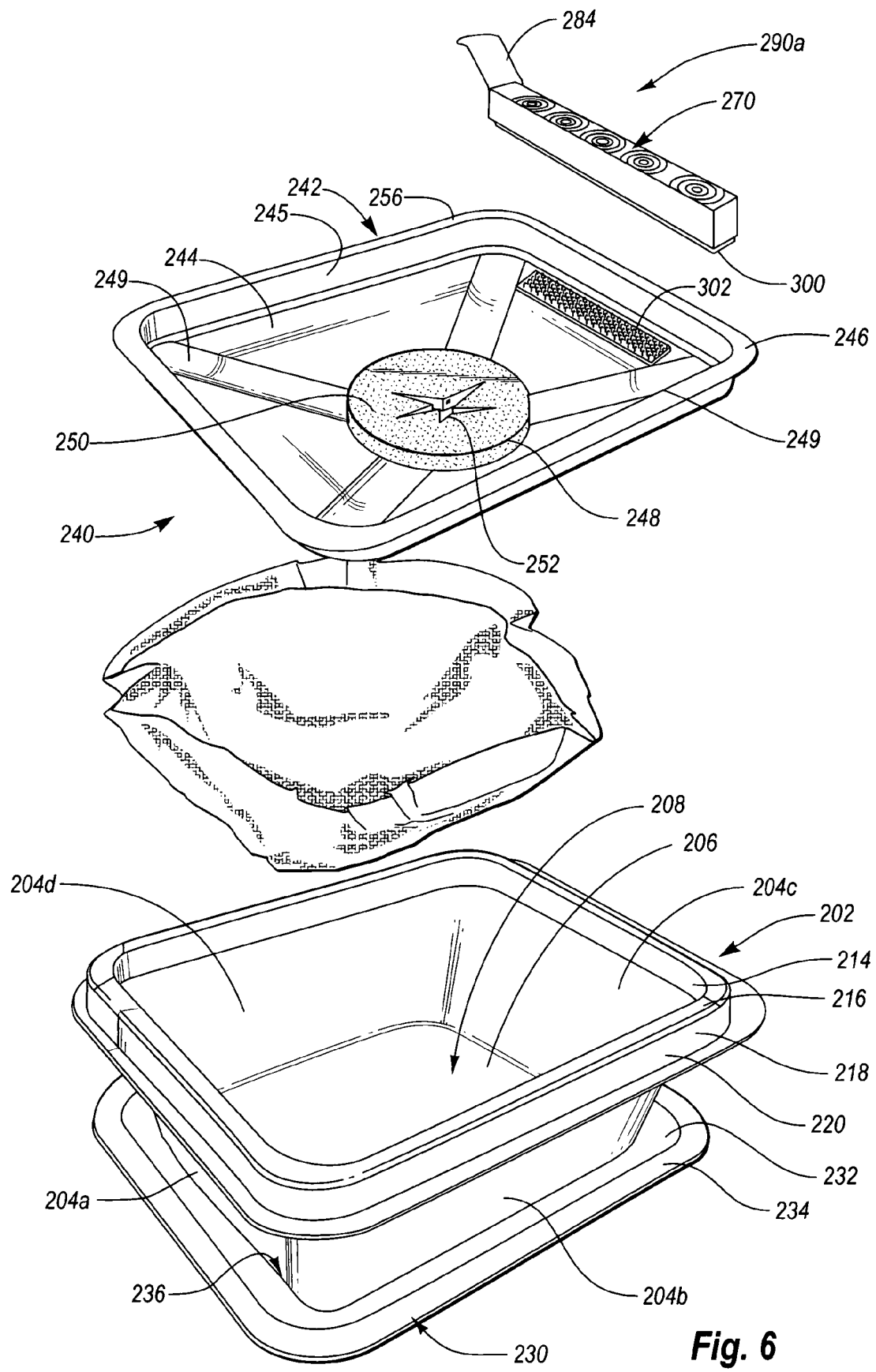
FIG. 6 illustrates an exploded perspective view of the components of the bio-waste container of FIG. 4 showing an alternate securement apparatus.

With reference now to FIG. 6, another alternate embodiment of a securement apparatus 290a is shown. All other details of this embodiment are identical to the embodiment shown in FIGS. 4 and 5. Securement apparatus 290a comprises a hook and loop type of temporary connection between needle stop device 270 and cover assembly 240. A hook element 300 can be attached to the underside of cushion element 272, while a loop element can be attached to surface 244 of container cover 242. One example of a hook and loop assembly that is well known in the art is Velcro®. In this exemplary embodiment, hook elements 300 engage loop elements 302 when the two are pressed together. The hook and loop elements then securely hold needle stop device 270 to cover assembly 240, until a sufficient force is applied to tab 284 to disengage hook elements 300 from loop elements 302. In this exemplary embodiment, top surface 244 of container cover 242 provides a puncture resistant layer to prevent needles and other sharp tipped objects from penetrating into container area 208.

In alternate exemplary embodiments, the position of the hook elements and loop elements can be reversed. In other alternate embodiments, the hook and loop elements can be attached to side 245 of container cover 242 and side 276a of cushion member 272. Any arrangement where cushion element 272 is releasably secured to cover assembly 240 is considered to be within the scope of this exemplary embodiment.

Figure 7:
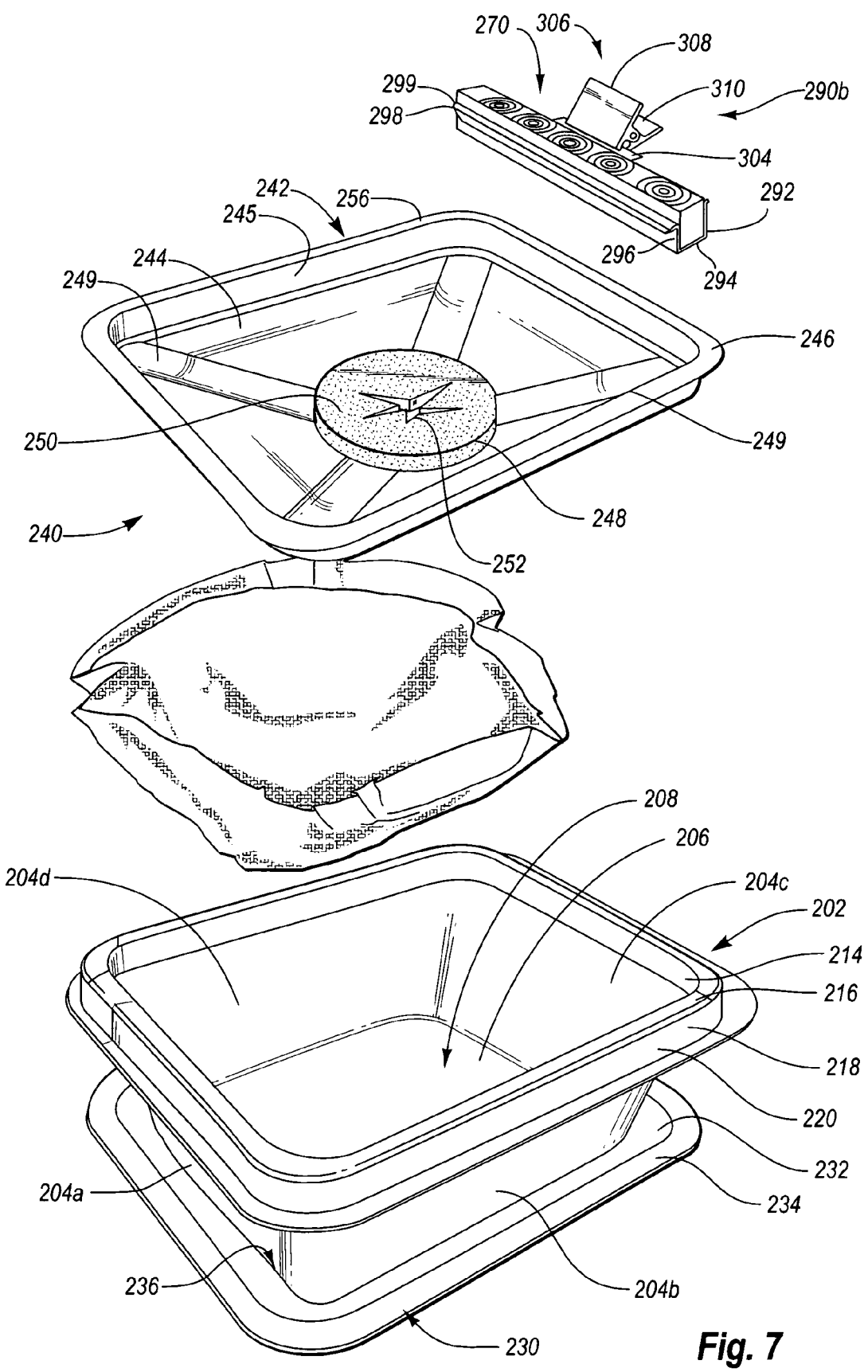
FIG. 7 illustrates an exploded perspective view of the components of the bio-waste container of FIG. 4 showing another alternate securement apparatus.

With reference now to FIG. 7, another alternate embodiment of a securement apparatus 290b is shown. In this alternate embodiment, the securement apparatus 290b is a shell, similar to securement apparatus 290 in FIGS. 4 and 5. The shell includes first side 292, bottom 294, second side 296 and curved portion 298 extending from second side 296. The curved portion 298, second side 296, and first side 292 define channel 299 that holds needle stop device 270. Securement apparatus 290b also includes an extension 304 of side 292. Integrated into extension 304 is a clip 306 that releasably secures the combination of the shell and needle stop device 290 to container cover 242. The clip 306 includes a first part 308 and a second part 310 that cooperates with first part 308 to secure securement apparatus 290b to container cover 242. In this embodiment, clip 306 is biased in the closed position by a spring (not shown).

The clip 306 can have first part 308 integrated into extension 304 of the side 292. Alternately, second part 310 can be integrated into lip 246 of container cover 242, or into ridge 212 of container portion 202. In still other alternate embodiments, clip 306 can be separate from both the shell, the cushion layer and the container portion. Other types of clips can also be used. For example, a paper clip type device can be used to temporarily secure the shell to container cover 242. Any type of a clip device that can releasably secure the shell, or cushion layer 272, to container cover 242 or container portion 202, is contemplated to fall within the scope of this embodiment.

In exemplary embodiments, clip 306 is made from plastic. The plastic of the clip can be integrated into either the shell, the container cover, or the container. In alternate embodiments, clip 306 can be made from metal or metal alloys, composites, or any other material capable of temporarily securing needle stop apparatus 270 to cover assembly 240.

Exemplary embodiments of the present invention provide some distinct advantages over prior systems. Since the medical waste container and needle stop device are an integrated unit, operating room personnel need only look in one place to dispose of the contaminated medical waste generated during a surgical procedure. This is true regardless of whether the waste is a used needle or a blood soaked sponge. Having the devices thus integrated provides a time saving alternative in the operating room. Additionally, having the needle stop device located adjacent the bio-waste container opening also allows for a more efficient use of space for any procedure, whether in an operating room, an emergency room, or some other location. Another advantage of the exemplary embodiments is that, when the needle stop device is removed from the container, the container can still function as a stand alone unit for the disposal of other contaminants.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An improved bio-waste container for use during a medical procedure, the bio-waste container comprising:
    a container portion comprising;
        a bottom;
        one or more sidewalls, the bottom and the one or more sidewalls defining a catch basin adapted to provide sufficient storage volume to accommodate the amount of blood, tissues, and other biological materials generated during a typical surgical procedure;
        a top section which extends around the perimeter of the container,
    a container cover removably secured to top section of the container portion, the container cover having an upper surface, a lower surface and an opening, the upper and lower surfaces having a downward slope which is inclined toward the interior of the container portion to facilitate the flow of fluids along the upper surface of the container cover, through the opening and into the catch basin, the container portion and the container cover defining a substantially enclosed interior space to minimizing splashing or spilling of the contents of the of the container portion during the course of the procedure; and
    a needle stop component comprising a puncture resistant layer and a cushion layer, the cushion layer being secured relative to the puncture resistant layer such that the needle stop component configured to accommodate needles and other sharp tipped objects so as to selectively retain said needles and other sharp tipped objects during the procedure,
    a securement mechanism for selectively coupling the needle stop component to one or both of the container portion and the container cover during shipping and use of the device but allowing the user to remove the needle stop component from one or both of the container portion and the container cover at the end of procedure permitting separate disposal of sharps positioned within the needle stop component and biological waste contained within the container portion.

2. The bio-waste container of claim 1, further comprising means for selectively securing the cushion portion to the container portion.

3. The bio-waste container of claim 1, wherein the means for selectively securing comprises a recess formed in the top of the container portion, the recess being configured to receive the cushion portion in press-fit nesting relationship.

4. The bio-waste container of claim 1, wherein the means for selectively securing comprises complementary hook and loop fasteners positioned on opposing surfaces of the cushion portion and the container portion.

5. The bio-waste container of claim 1, wherein means for selectively securing comprises an adhesive that holds said cushion portion to the container portion.

6. The bio-waste container of claim 1, further comprising a puncture resistant layer positioned at least on an underside of the cushion portion, the puncture resistant layer configured to prevent needles or other sharp tipped objects from penetrating into the interior space of the container portion.

7. The bio-waste container of claim 1, wherein the cushion portion can be selectively detached and discarded separately from the container portion.

8. The bio-waste container of claim 1, wherein said cushion portion is disposed of separately from said container portion.

9. The bio-waste container of claim 1, wherein the cushion portion comprises a resilient foam.

10. The bio-waste container of claim 1, wherein the cushion portion is non-coring.

11. The bio-waste container of claim 1, further comprising a lid configured to selectively engage the top of container portion in a press-fit relationship and so as to cover and seal off the contents contained within container portion for disposal.

12. The bio-waste container of claim 1, wherein the lid includes a recess to receive a bottom portion of the container portion in nesting relation during use.

13. A bio-waste disposal apparatus comprising:
a container comprising:
   a catch basin having a bottom and one or more sidewalls, the bottom and the one or more sidewalls configured to provide sufficient storage volume to accommodate the amount of blood, tissues, and other biological materials generated during a typical surgical procedure;
   a top section which extends around the perimeter of the container; and
   a cover assembly over said catch basin removably secured to the top section, the cover assembly having an upper surface and at least one opening therein to receive the bio-waste and secure the bio-waste within said catch basin, wherein the container portion and the container cover define a substantially enclosed interior space to minimizing splashing or spilling of the contents of the of the container portion during the course of the procedure, and wherein the upper surface has a downward slope inclined toward the interior of the container to facilitate the flow of fluids along the upper surface, through the opening and into the catch basin; and
a needle stop device attached to said container, said needle stop device comprising a cushion member for receiving and selectively retaining at least one needle or other sharp object therein, wherein said cushion member is removable such that said at least one needle or other sharp object can be disposed of separately from said container.

14. The bio-waste disposal apparatus of claim 13, wherein said needle stop device is removably attached to said cover assembly.

15. The bio-waste disposal apparatus of claim 13, wherein said cover assembly forms a puncture resistant layer for preventing needles or other sharps inserted into the cushion member from penetrating into the interior of the catch basin.

16. The bio-waste disposal apparatus of claim 13, wherein said cushion member comprises one of a plastic foam and a rubber compound.

17. The bio-waste disposal apparatus of claim 13, further comprising a puncture resistant layer interposed between said cushion member and said container.

18. The bio-waste disposal apparatus of claim 17, wherein said puncture resistant layer comprises a shell interposed between said cushion member and said container.

19. The bio-waste disposal apparatus of claim 18, wherein sad shell is secured to said cushion member.

20. An improved bio-waste container with integrated needle stop, intended for use during a medical procedure, comprising:
a container having a bottom, one or more sidewalls and a top and defining a substantially enclosed interior space configured to receive and hold the amount of bio-waste and other materials generated during a typical surgical procedure, the top of the container having an upper surface and an opening through which bio-waste and other materials can be deposited into the interior space during the course of the procedure, the upper surface having a downward slope which is inclined toward the interior of the container portion to facilitate the flow of fluids along the top, through the opening and into the interior space;
a needle stop comprising
   a cushion layer adapted to accommodate needles and other sharp tipped objects so as to secure said needles and other sharp tipped objects during the procedure; and
   a puncture resistant layer located beneath the cushion layer to prevent needles and other sharps from penetrating beyond the puncture resistant layer; and
   means for selectively securing the needle stop to the container in such a way that the needle stop is securely coupled to the container during shipping and use of the device but may be selectively removed from the container for disposal.

* * * * *